United States Patent
Sinclair et al.

(10) Patent No.: US 10,253,302 B2
(45) Date of Patent: Apr. 9, 2019

(54) METHOD FOR PRODUCING ORDERED PROTEIN LATTICE

(71) Applicant: Crysalin Ltd., London, Greater London (GB)

(72) Inventors: John Charles Sinclair, Oxford (GB); Ceri John Lewis, Linton (GB)

(73) Assignee: Crysalin Ltd., London, Greater London (GB)

( * ) Notice: Subject to any disclaimer, the term of this patent is extended or adjusted under 35 U.S.C. 154(b) by 0 days.

(21) Appl. No.: 14/913,038

(22) PCT Filed: Aug. 21, 2014

(86) PCT No.: PCT/GB2014/052565
§ 371 (c)(1),
(2) Date: Feb. 19, 2016

(87) PCT Pub. No.: WO2015/025167
PCT Pub. Date: Feb. 26, 2015

(65) Prior Publication Data
US 2016/0194614 A1 Jul. 7, 2016

(30) Foreign Application Priority Data
Aug. 21, 2013 (GB) .................................. 1314945.5

(51) Int. Cl.
C12N 9/04 (2006.01)
C07K 1/30 (2006.01)
B82Y 5/00 (2011.01)

(52) U.S. Cl.
CPC ............ *C12N 9/0006* (2013.01); *C07K 1/306* (2013.01); *C12Y 101/01086* (2013.01); *B82Y 5/00* (2013.01); *C07K 2319/40* (2013.01); *C07K 2319/70* (2013.01)

(58) Field of Classification Search
None
See application file for complete search history.

(56) References Cited

U.S. PATENT DOCUMENTS

| | | | | |
|---|---|---|---|---|
| 7,989,591 B2 * | 8/2011 | Sinclair | ................ | C07K 14/001 435/252.3 |
| 2010/0202672 A1 * | 8/2010 | Sinclair | ................ | C07K 14/001 382/128 |
| 2010/0329903 A1 | 12/2010 | Fong et al. | | |
| 2015/0053856 A1 | 2/2015 | Sinclair et al. | | |
| 2016/0194614 A1 * | 7/2016 | Sinclair | ................ | C12N 9/0006 435/190 |

FOREIGN PATENT DOCUMENTS

| | | |
|---|---|---|
| WO | WO 2004/033487 A1 | 4/2004 |
| WO | WO 2008/145951 A1 | 12/2008 |
| WO | WO 2010/019725 A2 | 2/2010 |
| WO | WO 2015/025167 A1 | 2/2015 |

OTHER PUBLICATIONS

Lapin et al. (J Phys. Chem. B., vol. 113, 2009, pp. 8776-8783).*
Ahn, H.J., et al., "Crystal Structure of Class I Acetohydroxy Acid Isomeroreductase from *Pseudomonas aeruginosa*", *J. Mol. Biol.* (2003) 328, 505-515.
Database Accession No. Q72JC8 sequence; Henne, A., et al., "The genome sequence of the extreme thermophile Thermus thermophiles"(Jul. 5, 2004), 2 pgs., XP-002731651.
International Search Report for International Application No. PCT/GB2014/052565, "Protein Crystals", dated Nov. 11, 2014.
Kim, K.K., "Crystal structure of a small heat-shock protein", *Letters to Nature*, 394: 595-599 (Aug. 1998).
Notification Concerning Transmittal of International Preliminary Report on Patentability for International Application No. PCT/GB2014/052565, "Protein Crystals", dated Feb. 23, 2016.
Sinclair, J.C., et al., "Generation of protein lattices by fusing proteins with matching rotational symmetry", *Nature Nanotechnology*, 6(9): 558-562 (Jul. 31, 2011).
Sinclair, J.C., et al., "Generation of protein lattices by fusing proteins with matching rotational symmetry", *Nature Nanotechnology*, 6: pp. 1-7 (Sep. 2011)—Supplementary Information.
Written Opinion for International Preliminary Report on Patentability for International Application No. PCT/GB2014/052565, "Protein Crystals", dated Nov. 11, 2014.
Zheng, J., et al., "From Molecular to Macroscopic via the Rational Design of a Self-Assembled 3D DNA Crystal", *Nature*, 461(7260): 74-77, doi: 10.1038/nature08274 (Mar. 3, 2010).

* cited by examiner

*Primary Examiner* — Hope Robinson
(74) *Attorney, Agent, or Firm* — Hamilton, Brook, Smith & Reynolds, P.C.

(57) ABSTRACT

A method for producing an ordered protein lattice, the method comprising: (a) providing a first component comprising a subunit of a homooligomeric protein assembly fused to a first subunit of a heterooligomeric protein assembly, and a second component comprising a second subunit of the heterooligomeric protein assembly, wherein the homooligomeric protein assembly and the heterooligomeric protein assembly are each symmetrical in two or three dimensions and share a rotational symmetry axis of the same order; (b) mixing said first monomer and said second monomer to produce a mixture; and (c1) (i) heating the mixture to a temperature about 2° C. to about 10° C. below the visible dissociation temperature; (ii) cooling the mixture by about 10° C. to about 20° C.; and (iii) repeating steps (i) and (ii) at least 10 times; or (c2) (i) heating the mixture to a temperature about 2° C. to about 30° C. or more below the visible dissociation temperature; and (ii) holding the mixture at a temperature about 2° C. to about 30° C. or more below the melt temperature, thereby producing an ordered protein lattice.

26 Claims, 2 Drawing Sheets
Specification includes a Sequence Listing.

METHOD FOR PRODUCING ORDERED PROTEIN LATTICE

RELATED APPLICATIONS

This application is the U.S. National Stage of International Application No. PCT/GB2014/052565, filed Aug. 21, 2014, which designates the U.S., published in English, and claims priority under 35 U.S.C. §§ 119 or 365(c) to GB Application No. 1314945.5, filed Aug. 21, 2013.

INCORPORATION BY REFERENCE OF MATERIAL IN ASCII TEXT FILE

This application incorporates by reference the Sequence Listing contained in the following ASCII text file:
a) File name: 53021000001 AmendedSequenceListing.txt; created Apr. 3, 2017, 30KB in size.

FIELD OF THE INVENTION

The present invention relates to ordered protein lattices having a regular structure repeating in two- or three-dimensions. The invention also relates to methods for producing such ordered protein lattices. The protein lattices are nanostructures which have many potential uses to which the invention also relates.

BACKGROUND TO THE INVENTION

The self assembly of supramolecular structures that are ordered on the nanometer scale is a key objective in nanotechnology. DNA and peptide nanotechnologies have produced various two- or three-dimensional structures, but protein molecules have been under exploited in this area of research.

It has been shown that genetic fusion of subunits from protein assemblies that have matching rotational symmetry generates species that can self-assemble in to well-ordered, pre-determined one-, two- and three-dimensional arrays that are stabilised by extensive intermolecular interactions. The supramolecular structures produced in this way are distinguished from protein crystals produced using conventional methods and are described in Sinclair et al. (2011) Nature Nanotechnology 6:558:562.

Supramolecular structures may be generated by the genetic fusion of peptide chains that derive from multi-subunit protein assemblies that have rotational symmetry axes of equal order. Binary structures are formed from discrete entities, termed "components". A binary structure comprises a first component formed by fusing a peptide chain from a homologous protein assembly (multi-subunit protein) to a peptide chain from a heterologous protein assembly (comprising two or more types of subunit). The second component of the binary structure comprises the second subunit from the heterologous protein assembly. When these complementary components are mixed, they self-assemble to form a supramolecular structure.

The components derived from multi-subunit protein assemblies naturally assemble to form regular lattices as a result of their neighbouring components being connected by two or more symmetrically equivalent interactions. As a consequence of this, the components are compelled to align along their common symmetry axis, imposing a fixed relative disposition of neighbouring subunits. Details of the required symmetries are disclosed in Sinclair et al., WO 2004/033487, and WO 2008/145951.

Sinclair et al. describe one-dimensional and two-dimensional protein lattices and disclose that the solid-phase materials produced using their preliminary designs for self-assembling binary three-dimensional lattices lack sufficient long-range order to permit study by X-ray diffraction. Therefore, there remains a need to develop methods to improve lattice order and facilitate the growth of larger crystals.

SUMMARY OF THE INVENTION

According to a first aspect, the invention provides a method for producing an ordered protein lattice, the method comprising: (a) providing a first component comprising a subunit of a homooligomeric protein assembly fused to a first subunit of a heterooligomeric protein assembly, and a second component comprising a second subunit of the heterooligomeric protein assembly, wherein the homooligomeric protein assembly and the heterooligomeric protein assembly are each symmetrical in two- or three-dimensions and share a rotational symmetry axis of the same order; (b) mixing said first component and said second component to produce a mixture; and (c1) (i) heating the mixture to a temperature about 2° C. to about 10° C. below the visible dissociation temperature; (ii) cooling the mixture by about 10° C. to about 20° C.; and (iii) repeating steps (i) and (ii) at least 10 times; or (c2) (i) heating the mixture to a temperature about 2° C. to about 30° C. below the visible dissociation temperature; and (ii) holding the mixture at a temperature about 2° C. to about 30° C. below the melt temperature, thereby producing an ordered protein lattice.

In further aspects, the invention provides:
an ordered protein lattice comprising: (i) a first component comprising a subunit of a thermostable homooligomeric protein assembly fused to a first subunit of a heterooligomeric protein assembly; and (ii) a second component comprising a second subunit of the heterooligomeric protein assembly, wherein the homooligomeric assembly and the heterooligomeric assembly are each symmetrical in two or three dimensions and share a rotational symmetry axis of the same order;
an ordered protein lattice comprising: (i) a first component comprising a subunit of dodecameric acetohydroxy acid isomeroreductase (AHIR) fused to a first subunit of a heterooligomeric protein assembly; and (ii) a second component comprising a second subunit of the heterooligomeric assembly, wherein the second homooligomeric assembly is symmetrical in two or three dimensions and shares a rotational symmetry axis of the same order as a rotational symmetry axis of the AHIR.
a polypeptide comprising a first component of an ordered protein lattice according to the invention;
a polynucleotide encoding a polypeptide according to the invention;
an expression vector comprising a polynucleotide according to the invention;
a host cell comprising an expression vector according to the invention; and
use of an ordered protein lattice of the invention in an method of biosensing or molecular imaging.

BRIEF DESCRIPTION OF THE SEQUENCE LISTING

Figure 1:
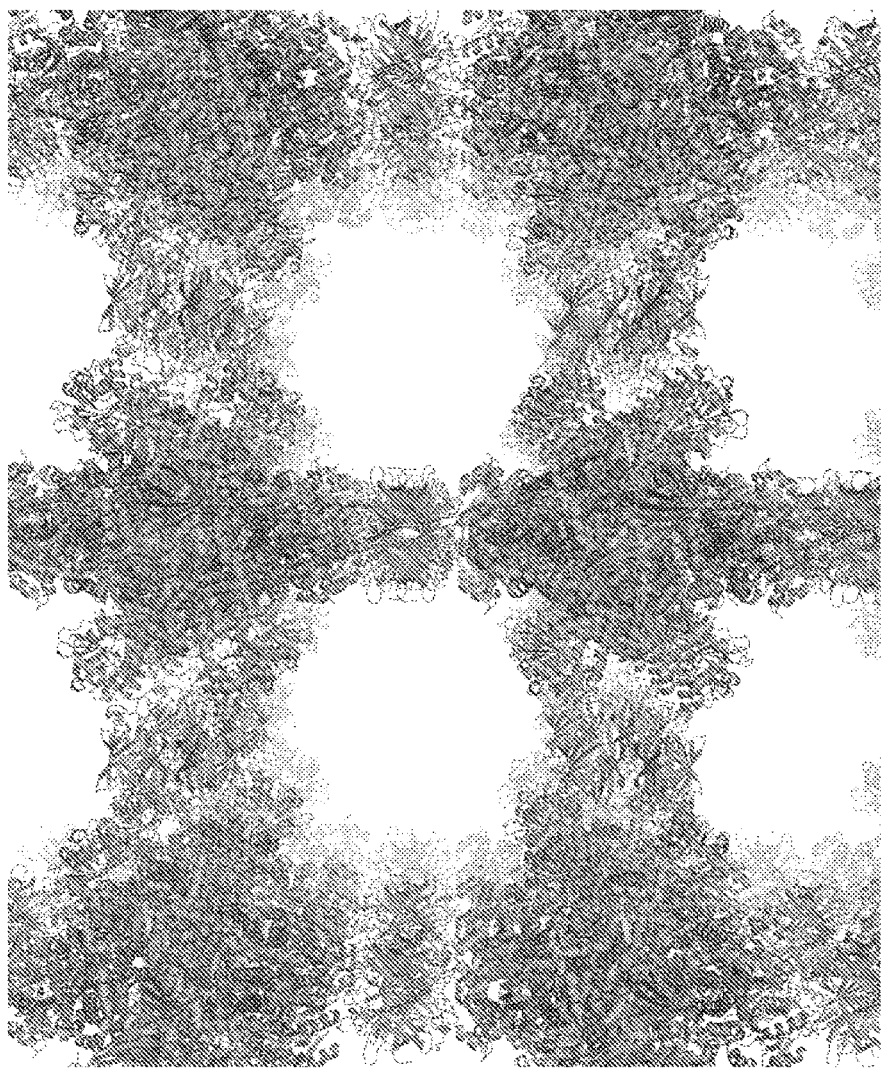
FIG. 1 is a picture of a crystal lattice in which the first component is AHIR fused to a Streptag peptide and the second component is Streptavidin.
Figure 2:
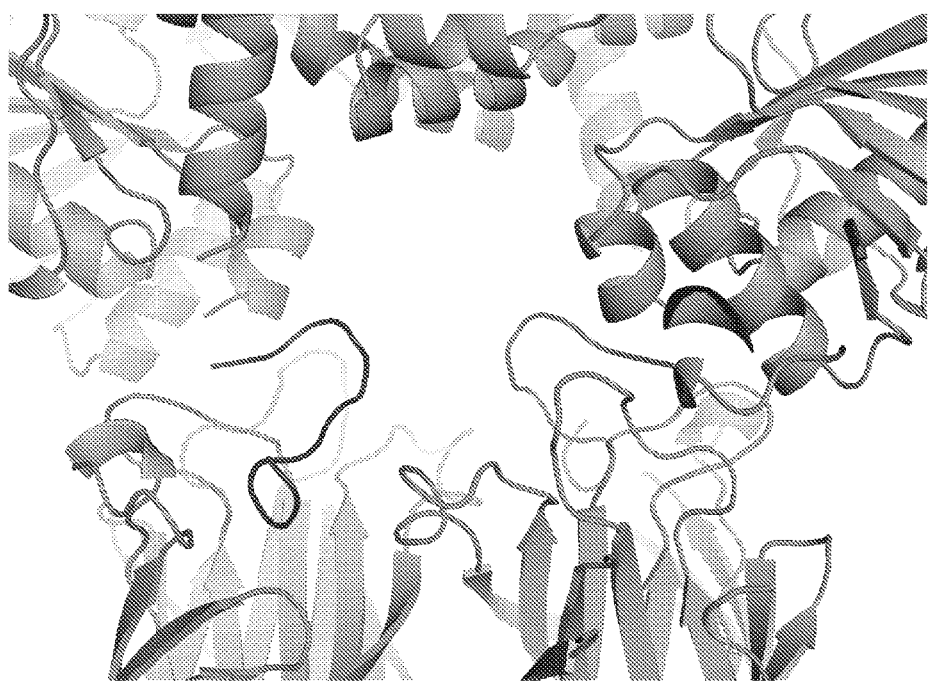
FIG. 2 shows details of the symmetric interaction between AHIR/Streptag and Streptavidin. The Streptag on the centre left of the picture is shown in dark shading. The symmetrical Streptag on the centre right is depicted in a lighter colour. AHIR, is shown at the top of the picture. Streptavidin is shown at the bottom.

SEQ ID NO: 1 is the amino acid sequence of an example of a component comprising a subunit of acetohydroxy acid isomeroreductase (AHIR) from *Thermus thermophilus* fused to a Streptag sequence. The first four and last two amino acids are vector derived. Residues 5 to 144 are residues 1 to 140 of AHIR. The Streptag sequence is at positions 149-157. Residues 162 to 344 are residues 143 to 325 of AHIR. Linker residues are present at positions 145-148 and 158-161.

SEQ ID NOs: 2 to 7 are further examples of components comprising a subunit of AHIR from *Thermus thermophilus* fused to a Streptag sequence.

SEQ ID NO: 8 is the sequence of the expression plasmid used to produce the exemplary component shown in SEQ ID NO: 1.

SEQ ID NO: 9 is the amino acid sequence of the standard Streptag II sequence.

SEQ ID NOs: 10 to 12 are amino acid sequences of examples of variant Streptag sequences.

SEQ ID NO: 13 is a consensus Streptag sequence.

SEQ ID NOs: 14 to 20 and 23 are examples of linker sequences which have four or more amino acids.

SEQ ID NO: 21 is the amino acid sequence of core Streptavidin.

SEQ ID NO: 22 is the Streptag binding motif.

DETAILED DESCRIPTION OF THE INVENTION

The invention provides a method for producing an ordered protein lattice. The ordered protein lattice comprises two components. The first component comprises a subunit of a homooligomeric protein assembly fused to a first subunit of a heterooligomeric protein assembly. The second component comprises a second subunit of the heterooligomeric protein assembly. The heterooligomeric protein assembly and the homooligomeric protein assembly are each symmetrical in two- or three-dimensions and share a rotational symmetry axis of the same order. In the first component, the second subunit of the heterooligomeric protein assembly may be fused to the subunit of the homooligomeric protein assembly close to the shared rotational symmetry axis.

The first and second components naturally assemble to form regular lattices as a result of neighbouring components being connected by two or more symmetrically equivalent interactions. As a consequence of this, components are compelled to align along their common symmetry axis, imposing a fixed relative disposition of neighbouring subunits.

Combinations of homologous and heterologous protein assemblies having compatible symmetries may be selected in accordance with the teachings of WO 2004/033487 and WO 2008/145951.

The subunit of the homologous protein assembly may be a naturally occurring sequence. Some modifications, such as deletion, substitution or addition of one or more, such as from about 2 to 300, 3 to 200, 5 to 100, 10 to 50, 12 to 30, or 15 to 20 amino acids, may be made to the subunit, provided that the subunit retains the ability to assemble into a homologous protein assembly. In one embodiment, an entire protein, or domain of a protein, other than the subunit of the heterologous protein assembly may be fused to the subunit of the homologous protein assembly. The deletions, substitutions and/or additions may be made at any site within the subunit, for example at the N- or C-terminus or at the site of insertion of the first subunit of the heterologous protein assembly. The subunit may be truncated at the N- and/or C-terminus and/or contain an internal deletion. The deleted amino acids are typically at the site of insertion of the first subunit of the heterooligomeric protein assembly, but modifications may also be made at other sites.

The homooligomeric assembly is advantageously a thermostable assembly. A thermostable homooligomeric protein is resistant to irreversible changes in its protein structure when heat is applied. The thermostable protein assembly is typically stable at temperatures above 50° C., such as temperatures 55° C., 60° C., 65° C., 70° C., 75° C., 80° C. or more.

Thermostable homooligomeric proteins are present in thermophilic organisms. Accordingly, the first component may comprise a subunit of a homooligomeric protein from a thermophilic organism such as *Thermus thermophilus, Pseudomonas aeruginosa, Azotobacter vinelandii, Saccrophagus degradans, Teredinibacter turnerae, Cellvibrio japonicas, Alcanivorax dieselolei, Thiothrix nivea, Meiothermus silvanus, Nitrococcus mobilis, Acidithiobacillus ferroxidans, Alkalilimnicola ehrlichei* or *Pelobacter propionicus*. Homooligomeric proteins in thermophilic organisms typically have homologues in other organisms that have only slight differences in the protein structure, such as the presence of extra hydrogen bonds in the thermostable protein. Therefore, proteins from other organisms may be used to derive the subunit of a homooligomeric protein assembly present in the first component. This will affect the temperature to which the component may be heated in the method of the invention.

One example of a homooligomeric protein assembly that may be used to derive the first component of the ordered protein lattice is acetohydroxy acid isomeroreductase (AHIR). AHIR is an enzyme involved in the synthesis of branch-chain amino acids. It is present in bacteria, fungi and plants, but not in animals. Different organisms have been shown to express AHIRs that assemble to one of two oligomeric forms: a dimer (class II, for example in spinach); or a dodecamer (class I, for example in *Pseudomonas aeruginosa*). For the purposes of the present invention, symmetry considerations mean that only AHIRs that assemble to a dodecameric form can be used. Structures of AHIR dodecamers that have been determined indicate that they are very similar in the way that they fold. Therefore, any dodecameric AHIR could be used to produce an ordered protein lattice of the invention, that may be produced using a method of the invention.

The first subunit of the heterooligomeric protein assembly may be fused internally within the AHIR sequence, typically at a site between residues 120 and 144 of AHIR using the numbering of AHIR from *Thermus thermophilus*, or the corresponding residues of AHIR from other organisms. Additional linker residues may be included at one or both ends of the inserted sequence of the first subunit of the heterooligomeric protein assembly.

The heterooligomeric protein assembly typically comprises two subunits. The assembly of the heterooligomeric protein occurs only when both subunits are present. The first subunit, which is fused to the subunit of the homooligomeric protein assembly in the first component, is typically a peptide. The second subunit of the heterooligomeric protein assembly that is present in the second component is typically a longer protein.

The peptide from the heterooligomeric assembly that is present in the first component may be, for example, from about 6 to about 20 amino acids in length, such as about 7 to 15 or 8 to 10 amino acids. The peptide sequence may be a naturally occurring sequence or may be a non-naturally occurring sequence. The peptide may contain a deletion, substitution and/or addition of one or more, such as 2 to 5, for example, 3 or 4 amino acids, provided that the peptide retains the ability to assemble into a heterooligomeric protein assembly together with the second subunit present in the second component.

The second subunit of the heterooligomeric protein assembly may be a naturally occurring or non-naturally occurring sequence. Some modifications, such as deletion, substitution and/or addition of one or more, such as from about 2 to 300, 3 to 200, 5 to 100, 10 to 50, 12 to 30 or 15 to 20 amino acids, may be made to the subunit, provided that the subunit retains the ability to assemble into a heterooligomeric assembly together with the first subunit present in the first component. In one embodiment, an entire protein, or domain of a protein, other than the subunit of the heterologous protein assembly may be fused to the subunit of the heterologous protein assembly. The deletions, substitutions and/or additions may be made at any site within the second subunit, for example at the N- or C-terminus or at a site within the second subunit of the heterologous protein assembly. Typically the subunit may be truncated at the N- and/or C-terminus.

A preferred heterooligomeric protein assembly comprises Streptag as the first subunit and Streptavidin as the second subunit. Typically, the Streptag is Streptag II. Streptag II is a peptide containing the motif "HPQ-" that has been found in vitro to bind to Streptavidin within the traditional biotin pocket. The standard Streptag II sequence is "WSHPQSEK" (SEQ ID NO: 9). This sequence may be varied by addition, deletion or substitution of one or more, such as 2, 3, 4 or 5 of the amino acids, provided that the core "HPQ" motif is maintained. The variant sequence is typically from 8 to 11 amino acids, such as 9 or 10 amino acids, in length. For example, the motif "SHPQ" (SEQ ID NO: 22) may be maintained and one, two, three or all of the other positions may be altered and/or an additional amino acid added. The "W" residue may, for example, be substituted by a "G", the "S" after the "Q" with an "F" and/or the "K" with a "G". A "P", "N" or "G" residue may be added at the N-terminus. Any combinations of these mutations may be made. A consensus Streptag sequence is shown in SEQ ID NO: 13. Particular examples of variant sequences are: NWSHPQFEK (SEQ ID NO: 10), PWSHPQFEK (SEQ ID NO: 11), and GGSHPQFEG (SEQ ID NO: 12).

Streptavidin is a naturally occurring tetrameric assembly with an extremely strong affinity for its biotin partner. Truncation of the full length sequence leaves Streptavidin functionally intact. The commonly truncated form of Streptavidin termed "core Streptavidin" is typically used. However, any Streptavidin variant with similar binding specificity and ability to form a tetrameric assembly may be used. The Streptavidin may comprise or consist of the sequence shown in SEQ ID NO: 21, or may comprise or consist of a sequence having at least 70%, such as at least 80%, at least 90% or at least 95% identity with SEQ ID NO: 21. Any mutations may be made, for example as detailed above, provided that the first component retains the ability to assemble into a tetrameric Streptavidin/Streptag assembly together with Streptavidin.

In the first component, the first subunit of the heterooligomeric protein assembly is fused to the subunit of the homooligomeric protein assembly either directly or using linker residues at one or both ends of the first subunit of the heterooligomeric protein assembly. A large number of linkers of different character and length have been used successfully. In one embodiment, the linkers are typically of between 1 and 10, preferably 2 and 5, such as 3 or 4, amino acids in length. The linkers may, for example, be composed of one or more of the following amino acids: lysine, serine, arginine, proline, glycine and alanine. Examples of suitable linkers include, but are not limited to, the following: GGGS (SEQ ID NO: 14), PGGS (SEQ ID NO: 23), PGGG (SEQ ID NO: 15), RPPPPP (SEQ ID NO: 16), RPPPP (SEQ ID NO: 17), VGG, RPPG (SEQ ID NO: 18), PPPP (SEQ ID NO: 19), RPPG (SEQ ID NO: 18), PPPPPPPP (SEQ ID NO: 20), RPPG (SEQ ID NO: 18), GG and GGG.

Appropriate linking groups may be designed using conventional modelling techniques. The linker is typically sufficiently flexible to allow the subunits to assemble into their respective protein assembly, but also sufficiently rigid so that the first and second components are compelled to align along their common symmetry axis in order to produce a regular structure within the protein lattice.

The first component and/or the second component may be modified in order to allow the incorporation of further proteins. Additional proteins or peptides may be attached to the first component and/or the second component. For example, a protein or peptide may be directly fused to the N-terminus or to the C-terminus of the subunit of the homooligomeric protein, or to the N-terminus or C-terminus of the second subunit of the heterooligomeric protein. A protein or peptide may also be fused between the subunit of the homologous protein assembly and the first subunit of the heterologous protein assembly in the first component. A portion of the sequence of the subunit of the homologous protein may be deleted to encompass the additional protein or peptide. The additional protein or peptide may be adjacent to the linker.

The first component and second component are typically expressed and purified independently using standard biochemical methods. The purified components are then mixed, typically in an aqueous solution. The solution typically has a pH between 6.5 and 9.0, preferably from 6.6 to 8.0, and an NaCl concentration of from 0 to 500 nM, preferably of from 0 to 150 mM. The aqueous solution may be phosphate buffered saline (PBS). Other suitable solutions include Tris, Bis Tris, Bis Tris Propane, MES, MOPS and HEPES.

Formation of an ordered lattice may be achieved at different ratios of the two components. Typically, the components are mixed at a ratio of 8 first components to 1 second component through to 1 first component to 8 second components, such as from 2 first components to 1 second component through to 1 first component to 4 second components. Ratios of excess second component are preferred. One example of a preferred ratio is 1 first component to 4 second components. This ratio is particularly advantageous where the homooligomeric protein assembly is a dodecamer and the heterooligomeric protein assembly is a tetramer.

It is preferred that the protein concentration in the mixture of first and second components is between about 1 and about 100 mg/ml, such as between about 5 and about 50 mg/ml, for example between about 10 and about 30 mg/ml.

When the two components are mixed at appropriate ratios and concentrations, precipitates are formed. These precipitates may be "dissolved" by heating. The temperature at which the precipitates disappear is referred to herein as the "visible dissociation temperature" or the "melt temperature".

The visible dissociation temperature will depend on the exact proteins used to prepare the first and second component. It will also be affected by the ratio at which the subunits are mixed.

In a method of the invention, the mixture of the two components is heated to the visible dissociation temperature, or to a temperature slightly below this temperature, the mixture may be heated to about 1° C. to 10° C. below the visible dissociation temperature, such as between about 2° C. to 8° C., 2° C. to 6° C. or 3° C. to 5° C. below the visible dissociation temperature. The mixture may be heated to a temperature that is more than 10° C. below the visible dissociation temperature, such as to a temperature that is 12° C., 15° C., 20° C. or 30° C. below the visible dissociation temperature.

Formation of an ordered protein lattice may then be promoted in one of two ways. The method of the invention comprises heating the mixture to within about 20° C. of the visible dissociation temperature; and then either repeatedly cooling the mixture by about 10° C. and reheating the mixture to within about 20° C. of the visible dissociation temperature, or heating the mixture to within about 20° C. or 30° C. holding the temperature of the mixture within about 20° C. or 30° C. of the visible dissociation temperature for an extended period, thereby producing an ordered protein lattice.

Thus, in one method, the temperature of the mixture is held constant at the elevated temperature. For example, the mixture is held at a temperature from about 2° C. to about 30° C., such as at a temperature of from about 5° C. to about 15° C. or about 6° C. to about 10° C. below the visible dissociation temperature. The elevated temperature is typically in the range of from about 20° C. (room temperature) to about 80° C., such as from about 30° C. to about 70° C., about 40° C. to about 65° C., about 45° C. to about 60° C., or about 50° C. to about 55° C. The temperature may be maintained at this elevated level for an extended period. This period may be from 1 hour to about 3 months, such as from about 2 hours to 2 months, 24 hours to 1 month or 2 weeks to 3 weeks. Generally the period for which the temperature is held constant is longer for lower temperatures. For example lattice formation occurs at room temperature but the lattice grows at a slower rate than when a higher temperature is used.

For protein lattices composed of AHIR and Streptavidin, cubic lattices with a diameter of more than 100 μm have been observed in less than 2 hours at a constant temperature of 55° C. Over a period of 24 hours, larger crystals have been produced.

The temperature may be held constant by any suitable means, for example in an incubator, heating block or thermocycler.

A second, effective method of promoting formation of an ordered protein lattice is thermocycling. Typically, this involves heating the mixture, for example to about 2° C. to 6° C. below the visible dissociation temperature and then lowering the temperature of the mixture before reheating the mixture to between 2° C. and 6° C. below the visible dissociation temperature then relowering the temperature and repeating this cycle. The temperature to which the mixture is lowered during this cycle is typically about 10° C. below the temperature to which the mixture is heated, i.e. to a temperature of about 12° C. to 16° C. below visible dissociation temperature. The difference between the highest temperature and the lowest temperature in the thermocycle may be more or less than 10° C. For example, it could be 6° C., 8° C., 12° C., 15° C., or 20° C. The cycle is typically repeated from about 10 to more than 1000 times, for example, 100, 500, 2000 or more times. The length of the cycle is typically from 2 seconds to 10 minutes, such as 30 seconds to 5 minutes or 1 minute to 2 minutes. The temperature of the mixture may be held at the high temperature and/or at the low temperature for a period of from about 1 second to about 5 minutes, for example from about 5 seconds to about 2 minutes, about 15 seconds to about 1 minute or about 30 seconds to about 45 seconds.

Typically, the cycle is repeated many times over a period of several hours, for example from 1 hour to 72 hours, such as from 2 hours to 48 hours, 12 hours to 24 hours or 16 hours to 20 hours.

In one embodiment, typically using AHIR and Streptavidin, the thermocycling involves oscillating for about 16 to about 72 hours over a temperature range of about 52° C. to 62° C. with a total period of approximately 1 minute, with 30 seconds at each of the high and low temperatures.

Thermocycling is typically carried out using a thermocycler.

The temperature at which protein lattices are formed may be increased or decreased by including additives in the mixture comprising the first and second components. Suitable additives which cause a reduction in temperature include glycerol, sucrose, salts and polyethylene glycols. Any other additives which affect the interaction between the first and second subunits of the heterooligomeric protein and hence between the first and second components, can cause a decrease or increase in the visible dissociation temperature. This will alter the temperature at which the ordered protein lattices are formed.

The present invention provides an ordered protein lattice comprising: (i) a first component comprising a subunit of a thermostable homooligomeric protein assembly fused to a first subunit of a heterooligomeric protein assembly, wherein the homooligomeric assembly and the heterooligomeric assembly are each symmetrical in two or three dimensions and share a rotational symmetry axis of the same order; and (ii) a second component comprising a second subunit of the heterooligomeric protein assembly.

The first and second components are typically assembled along the shared rotational symmetry axis with the subunits of the homologous protein assembly being assembled and the first and second subunits of the heterooligomeric protein assembly being assembled.

The invention also provides an ordered protein lattice comprising: (i) a first component comprising a subunit of a dodecameric AHIR fused to a first subunit of a heterooligomeric protein assembly, wherein the heterooligomeric assembly is symmetrical in two- or three-dimensions and shares a rotational symmetry axis with dodecameric AHIR; and (ii) a second component comprising a second subunit of the heterooligomeric protein assembly. Preferably, the heterooligomeric protein assembly is tetrameric. More preferably, the first subunit of the heterologous protein assembly is a peptide that binds to the biotin pocket in Streptavidin and the second subunit of the heterologous protein assembly is Streptavidin. The AHIR may be thermostable or thermosensitive.

The invention also provides a polypeptide which is a first component of the protein lattices of the invention. The polypeptide of the invention typically comprises the sequence of a subunit of a thermostable homooligomeric protein or AHIR fused to a first component of a heterooligomeric protein. The subunits of the thermostable homooligomeric protein or AHIR may comprise a naturally occurring sequence or a modified sequence as described above. The thermostable protein may be derived from a thermophilic organism as described above. The first component of a heterooligomeric protein is typically a peptide as described above.

In one particular embodiment, the polypeptide comprises the sequence shown in SEQ ID NO: 1. The polypeptide may comprise a sequence which is a variant of SEQ ID NO: 1. The variant may have at least 70%, such as at least 80%, at least 90% or at least 95% identity with SEQ ID NO: 1, or with any of SEQ ID NOs: 2 to 8. Any mutations may be made provided that the first component retains the ability to assemble into dodecameric AHIR and into a tetrameric Streptavidin/Streptag assembly together with Streptavidin. Such variants include corresponding parts of the AHIR subunit sequence from other organisms as described above, variant Streptag sequences that comprise the HPQ motif, and/or different linker residues as described above. Examples of variant sequences include: variants in which residues 132 to 140 of the AHIR sequence are deleted in addition to the deletion of residues 141 and 142 in SEQ ID NO: 1; variants in which the linker GGGS is replaced with the linker PGGG (SEQ ID NO: 15), RPPPPP (SEQ ID NO: 16), RPPPP (SEQ ID NO: 17) or VGG; variants in which the Streptag sequence is PWSHPQFEK (SEQ ID NO: 11), or GGSHPQFEG (SEQ ID NO: 12); and/or variants in which the linker RPPG (SEQ ID NO: 18) is replaced with the linker PPPP (SEQ ID NO: 19), RPPG (SEQ ID NO: 18), PPPP-PPPPP (SEQ ID NO: 20), GG or GGG. More specific examples that the inventors have used to produce crystal lattices are shown in SEQ ID NOs: 2 to 7 and detailed in Table 1.

TABLE 1

Examples of some successfully tested AHIR, Streptag and Linker sequences

| AHIR residues | Linker 1 | Streptag | Linker 2 | AHIR residues |
|---|---|---|---|---|
| 3-140 | -G-G-G-S- (SEQ ID NO: 14) | -N-W-S-H-P-Q-F-E-K- (SEQ ID NO: 10) | -R-P-P-G- (SEQ ID NO: 18) | 143-325 |
| 3-140 | -P-G-G-G- (SEQ ID NO: 15) | -P-W-S-H-P-Q-F-E-K- (SEQ ID NO: 11) | -P-P-P-P- (SEQ ID NO: 19) | 143-325 |
| 3-140 | -P-G-G-G- (SEQ ID NO: 15) | -P-W-S-H-P-Q-F-E-K- (SEQ ID NO: 11) | -R-P-P-G- (SEQ ID NO: 18) | 143-325 |
| 3-131 | -R-P-P-P-P-P (SEQ ID NO: 16) | -P-W-S-H-P-Q-F-E-K- (SEQ ID NO: 11) | -P-P-P-P-P-P-P-P-P- (SEQ ID NO: 20) | 143-325 |
| 3-131 | -R-P-P-P-P (SEQ ID NO: 17) | -P-W-S-H-P-Q-F-E-K- (SEQ ID NO: 11) | -R-P-P-G- (SEQ ID NO: 18) | 143-325 |
| 3-140 | -V-G-G- | -G-G-S-H-P-Q-F-E-G- (SEQ ID NO: 12) | -G-G- | 143-325 |
| 3-140 | -V-G-G- | -G-G-S-H-P-Q-F-E-G- (SEQ ID NO: 12) | -G-G-G- | 143-325 |

The invention also provides a polynucleotide which encodes the polypeptide of the invention. The polynucleotide may also comprise an additional sequence beyond the 5' and/or 3' ends of the coding sequence. The polynucleotide may be RNA or DNA, including genomic DNA, synthetic DNA or cDNA. The polynucleotide may be single or double stranded. A typical polynucleotide of the invention is shown in SEQ ID NO: 8.

The polynucleotide may comprise synthetic or modified nucleotides, such as methylphosphonate and phosphorothioate backbones or the addition of acridine or polylysine chains at the 3' and/or 5' ends of the molecule. Such polynucleotides may be produced and used using standard techniques.

The invention also provides expression vectors which comprise a polynucleotide of the invention and which are capable of expressing a first component of the invention. Such vectors may also comprise appropriate initiators, promoters, enhancers and other elements, such as for example polyadenylation signals which may be necessary, and which are positioned in the correct orientation, in order to allow for protein expression.

Thus the coding sequence in the vector is operably linked to such elements so that they provide for expression of the coding sequence (typically in a cell). The term "operably linked" refers to a juxtaposition wherein the components described are in a relationship permitting them to function in their intended manner.

The vector may be for example, plasmid, virus or phage vector. Typically the vector has an origin of replication. The vector may comprise one or more selectable marker genes, for example an ampicillin resistance gene in the case of a bacterial plasmid or a resistance gene for a fungal vector.

Promoters and other expression regulation signals may be selected to be compatible with the host cell for which expression is designed. For example, yeast promoters include *S. cerevisiae* GAL4 and ADH promoters, *S. pombe* nmt1 and adh promoter. Mammalian promoters include the metallothionein promoter which can be induced in response to heavy metals such as cadmium. Viral promoters such as the SV40 large T antigen promoter or adenovirus promoters may also be used.

Mammalian promoters, such as β-actin promoters, may be used. Tissue-specific promoters are especially preferred. Viral promoters may also be used, for example the Moloney murine leukaemia virus long terminal repeat (MMLV LTR), the rous sarcoma virus (RSV) LTR promoter, the SV40 promoter, the human cytomegalovirus (CMV) IE promoter, adenovirus, HSV promoters (such as the HSV IE promoters), or HPV promoters, particularly the HPV upstream regulatory region (URR).

Another method that can be used for the expression of the protein components is cell-free expression, for example bacterial, yeast or mammalian.

The invention also includes cells that have been modified to express the components of the invention. Such cells include transient, or preferably stable higher eukaryotic cell lines, such as mammalian cells or insect cells, using for example a baculovirus expression system, lower eukaryotic cells, such as yeast or prokaryotic cells such as bacterial cells. Particular examples of cells which may be modified by insertion of vectors encoding for a polypeptide according to the invention include mammalian HEK293T, CHO, HeLa and COS cells. Preferably the cell line selected will be one which is not only stable, but also allows for mature glycosylation of a polypeptide. Expression may be achieved in transformed oocytes.

The polypeptides, polynucleotides, vectors or cells of the invention may be present in a substantially isolated form. They may also be in a substantially purified form, in which case they will generally comprise at least 90%, e.g. at least 95%, 98% or 99%, of the proteins, polynucleotides, cells or dry mass of the preparation.

The components of the protein lattices may be prepared using vectors and host cells using standard techniques.

Protein lattices in accordance with the present invention have numerous different uses. The ordered protein lattices of the invention find utility where patterning on the nanometer scale is advantageous, especially where a regular array of guest molecules is required. In general, such uses will take advantage of the regular repeating structure and the pores within the lattice. Lattices in accordance with the present invention may be designed to have pores with dimensions expected to be of the order of nanometers to tens of nanometers. Lattices may be designed with an appropriate pore size for a desired use.

The highly defined, unusually sized and finely controlled pore sizes of the protein lattices together with the stability of their lattice structures make them ideal for applications requiring microporous materials with pore sizes in the range just mentioned. As one example, the lattices are expected to be useful as a filter element or molecular sieve for filtration or separation processes. In this use, the pore sizes achievable and the ability to design a pore's size would be particularly advantageous.

In another class of use, macromolecular entities would be attached to the protein lattice. Such attachment may be achieved using conventional techniques. The macromolecular entities may be any entities of an appropriate size, for example proteins, polynucleotides or non-biological entities. As such, the protein lattices are expected to be useful as biological matrices for carrying macromolecular entities, for example for use in drug delivery, or for crystallizing macromolecular entities.

Attachment of the macromolecular entities to the protein lattice may be performed by "tagging" either or both of the protein components or the macromolecular entities of interest. In this context, tagging is the covalent addition to either or both of the protein components or the target macromolecular entities, of a structure known as a tag which forms strong interactions with a target structure. The target structure may be a further tag attached to one of the components of the lattice or target macromolecular entity, or may be a part of the component or target macromolecular entity. In the case of the protein component, or a macromolecular entity which is a protein, this may be achieved by the expression of a genetically modified version of the protein to carry an additional sequence of peptide elements which constitute the tag, for example at one of its termini, or in a loop region. Alternative methods of adding a tag include covalent modification of a protein after it has been expressed, through techniques such as intein technology.

Thus to attach the macromolecular entity to the protein lattice, one or both of the protein components may include, at a predetermined position in the components, an affinity tag attached to the macromolecular entity of interest.

Alternatively, the macromolecular entity of interest may have at a predetermined position in one of the components, an affinity tag attached to a macromolecular entity.

When a component of the protein lattice is known to form strong interactions with a known peptide sequence, that peptide sequence may be used as a tag to be added to the target macromolecular entity. Where no such tight binding partner is known, suitable tags may be identified by means of screening. The types of screening possible are phage-display techniques, or redundant chemical library approaches to produce a large number of different short (for example 3-50 amino acids) peptides. The tightest binding peptide elements may be identified using standard techniques, for example amplification and sequencing in the case of phage-displayed libraries or by means of peptide sequencing in the case of redundant libraries.

To attach the macromolecular entity to the protein lattice using an affinity tag on the lattice or the macromolecular entity, the macromolecular entity may be allowed to diffuse into, and hence become attached to, a pre-formed protein lattice. For example, annealing of the bound macromolecular entity into its lowest energy configurations in the protein lattice may be performed using controlled cooling in a liquid nitrogen cryostream. Alternatively, the macromolecular entity may be mixed with the components during formation of the protein lattice to assemble with the lattice.

In another class of uses, proteins having useful properties could be incorporated as one of the subunits in one of the components.

The protein lattices of the invention may be used to facilitate the imaging of macromolecules and complexes that resist crystallisation.

A use in which an entity is attached to the protein lattice is to perform X-ray crystallography of the macromolecular entities. In this case, the regular structure of the protein lattice allows the macromolecular entities to be held in an array at a predetermined position relative to a repeating unit, so that they are held in a regular array and in a regular orientation. X-ray crystallography is important in biochemical research and rational drug design.

The protein lattice having an array of macromolecular entities supported thereof may be studied using standard X-ray crystallographic techniques. Use of the protein lattice as a support in X-ray crystallography is expected to provide numerous and significant advantages over current technology and protocol for X-ray crystallography, including the following:

(1) Significantly lower amounts of macromolecule will be required (probably of order micrograms rather than milligrams). This will allow determination of some previously intractable targets.
(2) Use of affinity tags will allow structure determination without the typical requirement for a number of purification steps.
(3) There will be no need to crystallize the macromolecular entity. This is a difficult and occasionally insurmountable step in traditional X-ray structure determination.
(4) There will be no need to obtain crystalline derivatives for each novel crystal structure to obtain the required phase information. Since the majority of scattering matter will be the known protein lattice in each case, determination of the structure may be automated and achieved rapidly by a computer user with little or no crystallographic expertise.
(5) The complexes of a protein with chemicals (substrates/drugs) and with other proteins can be examined without requiring entirely new crystallization conditions.
(6) The process is expected to be extremely rapid and universally applicable, which will provide enormous savings in time and costs.

For use in catalysing biotransformations, enzymes may be attached to the protein lattice, or incorporated in the protein lattice.

For use in data storage, it may be possible to attach a protein which is optically or electronically active. One example is Bacteriorhodopsin, but many other proteins can be used in this capacity. In this case, the protein lattice would hold the attached protein in a highly ordered array, thereby allowing the array to be addressed. The protein lattice is expected to be able to overcome the size limitations of existing matrices for holding proteins for use in data storage.

For use in a display, it may be possible to attach a protein which is photoactive or fluorescent. In this case, the protein lattice would hold the attached protein in a highly ordered array, thereby allowing the array to be addressed for displaying an image.

For use in charge separation, a protein which is capable of carrying out a charge separation process may be attached to the protein lattice, or incorporated in the protein lattice. Then the protein may be induced to carry out the separation, for example biochemically by a "fuel" such as ATP or optically in the case of a photoactive centre such as chlorophyll or a photoactive protein such as rhodopsin. A variety of charge separation processes might be performed in this way, for example ion pumping or development of a photo-voltaic charge.

For use as a nanowire, a protein which is capable of electrical conduction may be attached to the protein lattice, or incorporated in the protein lattice. Using an anisotropic protein lattice, it might be able to provide the capability of carrying current in a particular direction.

For use as a motor, proteins which are capable of induced expansion/contraction may be incorporated into the protein lattice.

The protein lattices may be used as a mould. For example, silicon could be diffused or otherwise impregnated into the pores of the protein lattice, thus either partially or completely filling the lattice interstices. The protein material comprising the original lattice may, if required, then be removed, for example, through the use of a hydrolysing solution.

The ordered lattices may be used to capture nanoparticles, such as gold nanoparticles, and be used in optical and electronic circuitry or in biosensing methods.

The invention is illustrated in the following Examples.

EXAMPLES

Example 1

Fusion Construct Generation

One consistently successful example of an AHIR-Streptag fusion, designated LC4, has the amino acid sequence:

(SEQ ID NO: 1)
MTGTMKIYYEHDADLGFILGKKVAVLGFGSQGHAHALNLKDSGVDVRVG

LRKGSRSWEKAEAAGLRVLPVAEAVREADVVMVLLPDEKQAQVYREEVE

PNLKEGGALAFAHGFNVHFGQIKPRKDLDVWMVAPKGPGHLVRSEYGGG

SNWSHPQFEKRPPGGSGVPALVAVHQDASGSAFPTALAYAKAIGAARAG

VIATTFKDETETDLFGEQAVLCGGLTRLIRAGFETLVEAGYPPEMAYFE

TVHEVKLIVDLIYEAGLKGMRYSISNTAEYGDYTRGDLAVPLEETKRRM

REILRQIQSGEFAREWMLENQVGSPVLEANRKRWAAHPIEEVGSRLRAM

MRS

Underlined only sequences are vector derived, Bold only sequences are linker sequences, and the BoldUnderlined sequence is Streptag II. The remaining sequence is *Thermus thermophilus* AHIR residues 1-325. This portion of the AHIR gene was cloned from *Thermus thermophilus* genomic DNA into a pUC-19 derived plasmid before insertion of the Streptag II and linker sequence between residues 140 and 143. All cloning was accomplished using standard molecular biology techniques. The vector sequence is shown in SEQ ID NO: 2.

Expression

Expression of LC4 protein was accomplished by inoculation of a single colony of *E. coli* (strain BL21 star (DE3), but other strains could be used) into between 10 mls and 1 liter of LB broth followed by an overnight incubation (typically 16 hrs, 37° C.).

Purification

Cultures were harvested (5000 g, 5 min) and lysed by sonication into ⅕₀th culture volume of phosphate buffered saline (PBS).

Purification of LC4 from crude lysate has been accomplished successfully by two distinct routes, although other standard biochemical purification methods are also possible.

Strategy 1
1) The lysate was heated (65° C., 30 min) and pelleted (5000 g, 20 min);
2) Three ammonium sulphate cuts were performed, in each case taking the fraction precipitating at 25% saturation (22° C.) was taken and resuspended in 5 ml PBS;
3) The resuspended solution was fractionated on a superose 6 size exclusion column, eluting in PBS, and the peak corresponding to the 453 kDa dodecamer was pooled and concentrated as required.

Strategy 2
1) The lysate was clarified (50,000 g, 30 min, 4° C.);
2) Clarified lysate was applied to a streptactin column (GE Healthcare) and eluted using desthiobiotin as per the manufacturer's instructions;
3) The eluted protein was fractionated on a superose 6 size exclusion column, eluted in PBS, and the peak corresponding to the 453 kDa dodecamer was pooled and concentrated as required.

Streptavidin

Core Streptavidin was purchased from IBA (www.iba-life-sciences.com/details/product/2.html) in purified form.

Example 2

3D Lattice Formation

Precipitates formed by the combination Strep tagged AHIR and Streptavidin were "dissolved" by heating. The exact temperature at which the precipitates disappeared varied with the precise construct—but in PBS (Dulbecco A phosphate buffered saline) was typically in the 60-70° C. region. For LC4 formed from 1:1 subunit ratio with Streptavidin the temperature at which visible dissociation occurred was between 63° C. and 65° C. This temperature we call the melt temperature.

Optimal lattice formation with LC4 occurs at elevated temperatures (greater than 50° C.). This temperature may either be constant (e.g. in an incubator, heating block or thermocycler) or repeatedly cycled between high and low temperatures (using a thermocycler).

Purified LC4 was mixed (typically to give a final concentration of between 5 and 20 mg/ml) with core Streptavidin in PBS. The optimal molar ratio of LC4 to Streptavidin was approximately 1 LC4 (dodecamer) to 4 Streptavidin (tetramers), i.e. a ratio of 3 first components to 4 second components. However successful lattice formation has been achieved at ratios both lower and higher than this.

Cubic lattices >100 μm were observed in <2 hours at a constant temperature of 55° C. Growth for 24 hours produced larger crystals.

Thermal cycling involves oscillating for 4-72 hours over a temperature range (typically 52° C.-62° C.) with a total period of approximately 1 minute (30 seconds each at the high and low temperatures) per cycle.

Both strategies have been used to produce lattices with linear dimensions up to 0.5 mm.

The invention claimed is:

1. A method for producing an ordered protein lattice, the method comprising:
   (a) providing a first component comprising a subunit of a homooligomeric protein assembly, wherein the homooligomeric protein assembly is dodecameric acetohydroxy acid isomeroreductase (AHIR), fused to a first subunit of a heterooligomeric protein assembly, wherein the first subunit of the heterooligomeric protein is a Streptag peptide of from 8 to 11 amino acids in length comprising a histidine-proline-glutamine (HPO) motif and that binds to the biotin binding site in Streptavidin, and a second component comprising a second subunit of the heterooligomeric protein assembly, wherein the second subunit of the heterooligomeric protein is Streptavidin, and wherein the homooligomeric protein assembly and the heterooligomeric protein assembly are each symmetrical in two or three dimensions and share a rotational symmetry axis of the same order;
   (b) mixing said first component and said second component to produce a mixture;
   (c) heating the mixture to a temperature about 2° C. to about 10° C. below a temperature at which precipitates that are present in the mixture disappear, wherein said temperature is a visible dissociation temperature;
   (d) cooling the mixture by about 10° C. to about 20° C.; and
   (e) repeating (c) and (d) at least 10 times, thereby producing an ordered protein lattice.

2. The method according to claim 1, wherein the homooligomeric protein is thermostable above 50° C.

3. The method according to claim 1, wherein each of (c) and (d) is 5 seconds or longer.

4. The method according to claim 1, wherein the mixture comprises one or more additives that reduce the visible dissociation temperature.

5. The method according to claim 1, wherein the mixture has a protein concentration of from about 1 to 100 mg/ml.

6. The method according to claim 1, wherein in (b) the first component and second component are mixed at a ratio of from 8:1 to 1:8.

7. The method according to claim 1, wherein the homooligomeric protein assembly is obtained from a thermophilic organism.

8. The method according to claim 1, wherein the Streptag peptide comprises the amino acid sequence of SEQ ID NO: 13.

9. The method according to claim 1, wherein the Streptag peptide comprises an amino acid sequence selected from the group consisting of SEQ ID NOs: 9, 10, 11 and 12.

10. The method according to claim 1, wherein the Streptag peptide is linked to the subunit of the homooligomeric protein by from 2 to 6 linking amino acids at one or both ends of the peptide.

11. The method according to claim 1, wherein the first subunit of the heterooligomeric protein assembly is fused internally within the amino acid sequence of the subunit of the homooligomeric protein.

12. The method according to claim 1, wherein the first component comprises an amino acid sequence selected from the group consisting of SEQ ID NOs: 1, 2, 3, 4, 5, 6, 7 and 8.

13. A method for producing an ordered protein lattice, the method comprising:
   (a) providing a first component comprising a subunit of a homooligomeric protein assembly, wherein the homooligomeric protein assembly is dodecameric acetohydroxy acid isomeroreductase (AHIR), fused to a first subunit of a heterooligomeric protein assembly, wherein the first subunit of the heterooligomeric protein is a Streptag peptide of from 8 to 11 amino acids in length comprising a histidine-proline-glutamine (HPQ) motif and that binds to the biotin binding site in Streptavidin, and a second component comprising a second subunit of the heterooligomeric protein assembly, wherein the second subunit of the heterooligomeric protein is Streptavidin, and wherein the homooligomeric protein assembly and the heterooligomeric protein assembly are each symmetrical in two or three dimensions and share a rotational symmetry axis of the same order;
   (b) mixing said first component and said second component to produce a mixture;
   (c) determining the temperature at which precipitates present in the mixture disappear, wherein said temperature is a visible dissociation temperature;
   (d) heating the mixture to a temperature about 2° C. to about 10° C. below the visible dissociation temperature;
   (e) cooling the mixture by about 10 ° C. to about 20 ° C.; and
   (f) repeating steps (d) and (e) at least 10 times,
   thereby producing an ordered protein lattice.

14. A method for producing an ordered protein lattice, the method comprising:
   (a) providing a first component comprising a subunit of a homooligomeric protein assembly, wherein the homooligomeric protein assembly is dodecameric acetohydroxy acid isomeroreductase (AHIR), fused to a first subunit of a heterooligomeric protein assembly, wherein the first subunit of the heterooligomeric protein is a Streptag peptide of from 8 to 11 amino acids in length comprising a histidine-proline-glutamine (HPQ) motif and that binds to the biotin binding site in Streptavidin, and a second component comprising a second subunit of the heterooligomeric protein assembly, wherein the second subunit of the heterooligomeric protein is Streptavidin, and wherein the homooligomeric protein assembly and the heterooligomeric protein assembly are each symmetrical in two or three dimensions and share a rotational symmetry axis of the same order;
   (b) mixing said first component and said second component to produce a mixture;
   (c) heating the mixture to a temperature about 2° C. to about 30° C. or more below the visible dissociation temperature; and
   (d) holding the mixture at a temperature about 2° C. to about 30° C. or more below the visible dissociation temperature,
   thereby producing an ordered protein lattice.

15. The method according to claim 14, wherein the homooligomeric protein is thermostable above 50° C.

16. The method according to claim 14, wherein in (d) the temperature is kept constant for about 1 hour to about 3 months.

17. The method according to claim 14, wherein the mixture comprises one or more additives that reduce the visible dissociation temperature.

18. The method according to claim 14, wherein the mixture has a protein concentration of from about 1 to 100 mg/ml.

19. The method according to claim 14, wherein in (b) the first component and second component are mixed at a ratio of from 8:1 to 1:8.

20. The method according to claim 14, wherein the homooligomeric protein assembly is obtained from a thermophilic organism.

21. The method according to claim 14, wherein the Streptag peptide comprises the amino acid sequence of SEQ ID NO: 13.

22. The method according to claim 14, wherein the Streptag peptide comprises an amino acid sequence selected from the group consisting of SEQ ID NOs: 9, 10, 11 and 12.

23. The method according to claim 14, wherein the Streptag peptide is linked to the subunit of the homooligomeric protein by from 2 to 6 linking amino acids at one or both ends of the peptide.

24. The method according to claim 14, wherein the first subunit of the heterooligomeric protein assembly is fused internally within the amino acid sequence of the subunit of the homooligomeric protein.

25. The method according to claim 14, wherein the first component comprises an amino acid sequence selected from the group consisting of SEQ ID NOs: 1, 2, 3, 4, 5, 6, 7 and 8.

26. A method for producing an ordered protein lattice, the method comprising:
   (a) providing a first component comprising a subunit of a homooligomeric protein assembly, wherein the homooligomeric protein assembly is dodecameric acetohydroxy acid isomeroreductase (AHIR), fused to a first subunit of a heterooligomeric protein assembly, wherein the first subunit of the heterooligomeric protein is a Streptag peptide of from 8 to 11 amino acids in length comprising a histidine-proline-glutamine (HPQ) motif and that binds to the biotin binding site in Streptavidin, and a second component comprising a second subunit of the heterooligomeric protein assembly, wherein the second subunit of the heterooligomeric protein is Streptavidin, and wherein the homooligomeric protein assembly and the heterooligomeric protein assembly are each symmetrical in two or three dimensions and share a rotational symmetry axis of the same order;
   (b) mixing said first component and said second component to produce a mixture;
   (c) determining the temperature at which precipitates present in the mixture disappear, wherein said temperature is a visible dissociation temperature;
   (d) heating the mixture to a temperature about 2° C. to about 30° C. or more below the visible dissociation temperature; and
   (e) holding the mixture at a temperature about 2° C. to about 30° C. or more below the visible dissociation temperature, thereby producing an ordered protein lattice.

* * * * *

UNITED STATES PATENT AND TRADEMARK OFFICE
CERTIFICATE OF CORRECTION

PATENT NO. : 10,253,302 B2
APPLICATION NO. : 14/913038
DATED : April 9, 2019
INVENTOR(S) : John Charles Sinclair et al.

It is certified that error appears in the above-identified patent and that said Letters Patent is hereby corrected as shown below:

In the Claims

In Column 37, Claim 1, Line 49, delete "(HPO)" and insert -- (HPQ) --

Signed and Sealed this
Eighteenth Day of June, 2019

Andrei Iancu
*Director of the United States Patent and Trademark Office*

SEQUENCE LISTING

<160> NUMBER OF SEQ ID NOS: 23

<210> SEQ ID NO 1
<211> LENGTH: 346
<212> TYPE: PRT
<213> ORGANISM: Artificial Sequence
<220> FEATURE:
<223> OTHER INFORMATION: COMPONENT OF LATTICE

<400> SEQUENCE: 1

```
Met Thr Gly Thr Met Lys Ile Tyr Tyr Glu His Asp Ala Asp Leu Gly
1               5                   10                  15

Phe Ile Leu Gly Lys Lys Val Ala Val Leu Gly Phe Gly Ser Gln Gly
                20                  25                  30

His Ala His Ala Leu Asn Leu Lys Asp Ser Gly Val Asp Val Arg Val
            35                  40                  45

Gly Leu Arg Lys Gly Ser Arg Ser Trp Glu Lys Ala Glu Ala Ala Gly
        50                  55                  60

Leu Arg Val Leu Pro Val Ala Glu Ala Val Arg Glu Ala Asp Val Val
65                  70                  75                  80

Met Val Leu Leu Pro Asp Glu Lys Gln Ala Gln Val Tyr Arg Glu Glu
                85                  90                  95

Val Glu Pro Asn Leu Lys Glu Gly Ala Leu Ala Phe Ala His Gly
                100                 105                 110

Phe Asn Val His Phe Gly Gln Ile Lys Pro Arg Lys Asp Leu Asp Val
            115                 120                 125

Trp Met Val Ala Pro Lys Gly Pro Gly His Leu Val Arg Ser Glu Tyr
        130                 135                 140

Gly Gly Gly Ser Asn Trp Ser His Pro Gln Phe Glu Lys Arg Pro Pro
145                 150                 155                 160

Gly Gly Ser Gly Val Pro Ala Leu Val Ala Val His Gln Asp Ala Ser
                165                 170                 175

Gly Ser Ala Phe Pro Thr Ala Leu Ala Tyr Ala Lys Ala Ile Gly Ala
            180                 185                 190

Ala Arg Ala Gly Val Ile Ala Thr Thr Phe Lys Asp Glu Thr Glu Thr
        195                 200                 205

Asp Leu Phe Gly Glu Gln Ala Val Leu Cys Gly Gly Leu Thr Arg Leu
    210                 215                 220

Ile Arg Ala Gly Phe Glu Thr Leu Val Glu Ala Gly Tyr Pro Pro Glu
225                 230                 235                 240

Met Ala Tyr Phe Glu Thr Val His Glu Val Lys Leu Ile Val Asp Leu
                245                 250                 255

Ile Tyr Glu Ala Gly Leu Lys Gly Met Arg Tyr Ser Ile Ser Asn Thr
            260                 265                 270

Ala Glu Tyr Gly Asp Tyr Thr Arg Gly Asp Leu Ala Val Pro Leu Glu
        275                 280                 285

Glu Thr Lys Arg Arg Met Arg Glu Ile Leu Arg Gln Ile Gln Ser Gly
    290                 295                 300

Glu Phe Ala Arg Glu Trp Met Leu Glu Asn Gln Val Gly Ser Pro Val
305                 310                 315                 320

Leu Glu Ala Asn Arg Lys Arg Trp Ala Ala His Pro Ile Glu Glu Val
                325                 330                 335

Gly Ser Arg Leu Arg Ala Met Met Arg Ser
            340                 345
```

-continued

<210> SEQ ID NO 2
<211> LENGTH: 340
<212> TYPE: PRT
<213> ORGANISM: Artificial Sequence
<220> FEATURE:
<223> OTHER INFORMATION: COMPONENT OF LATTICE

<400> SEQUENCE: 2

```
Met Lys Ile Tyr Tyr Glu His Asp Ala Asp Leu Gly Phe Ile Leu Gly
1               5                  10                  15

Lys Lys Val Ala Val Leu Gly Phe Gly Ser Gln Gly His Ala His Ala
            20                  25                  30

Leu Asn Leu Lys Asp Ser Gly Val Asp Val Arg Val Gly Leu Arg Lys
        35                  40                  45

Gly Ser Arg Ser Trp Glu Lys Ala Glu Ala Ala Gly Leu Arg Val Leu
    50                  55                  60

Pro Val Ala Glu Ala Val Arg Glu Ala Asp Val Val Met Val Leu Leu
65                  70                  75                  80

Pro Asp Glu Lys Gln Ala Gln Val Tyr Arg Glu Glu Val Glu Pro Asn
                85                  90                  95

Leu Lys Glu Gly Gly Ala Leu Ala Phe Ala His Gly Phe Asn Val His
            100                 105                 110

Phe Gly Gln Ile Lys Pro Arg Lys Asp Leu Asp Val Trp Met Val Ala
        115                 120                 125

Pro Lys Gly Pro Gly His Leu Val Arg Ser Glu Tyr Pro Gly Gly Gly
    130                 135                 140

Pro Trp Ser His Pro Gln Phe Glu Lys Pro Pro Pro Gly Ser Gly
145                 150                 155                 160

Val Pro Ala Leu Val Ala Val His Gln Asp Ala Ser Gly Ser Ala Phe
                165                 170                 175

Pro Thr Ala Leu Ala Tyr Ala Lys Ala Ile Gly Ala Ala Arg Ala Gly
            180                 185                 190

Val Ile Ala Thr Thr Phe Lys Asp Glu Thr Glu Thr Asp Leu Phe Gly
        195                 200                 205

Glu Gln Ala Val Leu Cys Gly Gly Leu Thr Arg Leu Ile Arg Ala Gly
    210                 215                 220

Phe Glu Thr Leu Val Glu Ala Gly Tyr Pro Pro Glu Met Ala Tyr Phe
225                 230                 235                 240

Glu Thr Val His Glu Val Lys Leu Ile Val Asp Leu Ile Tyr Glu Ala
                245                 250                 255

Gly Leu Lys Gly Met Arg Tyr Ser Ile Ser Asn Thr Ala Glu Tyr Gly
            260                 265                 270

Asp Tyr Thr Arg Gly Asp Leu Ala Val Pro Leu Glu Glu Thr Lys Arg
        275                 280                 285

Arg Met Arg Glu Ile Leu Arg Gln Ile Gln Ser Gly Glu Phe Ala Arg
    290                 295                 300

Glu Trp Met Leu Glu Asn Gln Val Gly Ser Pro Val Leu Glu Ala Asn
305                 310                 315                 320

Arg Lys Arg Trp Ala Ala His Pro Ile Glu Glu Val Gly Ser Arg Leu
                325                 330                 335

Arg Ala Met Met
            340
```

<210> SEQ ID NO 3
<211> LENGTH: 340
<212> TYPE: PRT
<213> ORGANISM: Artificial Sequence
<220> FEATURE:
<223> OTHER INFORMATION: COMPONENT OF LATTICE

<400> SEQUENCE: 3

Met Lys Ile Tyr Tyr Glu His Asp Ala Asp Leu Gly Phe Ile Leu Gly
1               5                   10                  15

Lys Lys Val Ala Val Leu Gly Phe Gly Ser Gln Gly His Ala His Ala
            20                  25                  30

Leu Asn Leu Lys Asp Ser Gly Val Asp Val Arg Val Gly Leu Arg Lys
        35                  40                  45

Gly Ser Arg Ser Trp Glu Lys Ala Glu Ala Ala Gly Leu Arg Val Leu
    50                  55                  60

Pro Val Ala Glu Ala Val Arg Glu Ala Asp Val Val Met Val Leu Leu
65                  70                  75                  80

Pro Asp Glu Lys Gln Ala Gln Val Tyr Arg Glu Glu Val Glu Pro Asn
                85                  90                  95

Leu Lys Glu Gly Gly Ala Leu Ala Phe Ala His Gly Phe Asn Val His
            100                 105                 110

Phe Gly Gln Ile Lys Pro Arg Lys Asp Leu Asp Val Trp Met Val Ala
        115                 120                 125

Pro Lys Gly Pro Gly His Leu Val Arg Ser Glu Tyr Pro Gly Gly Gly
    130                 135                 140

Pro Trp Ser His Pro Gln Phe Glu Lys Arg Pro Pro Gly Gly Ser Gly
145                 150                 155                 160

Val Pro Ala Leu Val Ala Val His Gln Asp Ala Ser Gly Ser Ala Phe
                165                 170                 175

Pro Thr Ala Leu Ala Tyr Ala Lys Ala Ile Gly Ala Ala Arg Ala Gly
            180                 185                 190

Val Ile Ala Thr Thr Phe Lys Asp Glu Thr Glu Thr Asp Leu Phe Gly
        195                 200                 205

Glu Gln Ala Val Leu Cys Gly Gly Leu Thr Arg Leu Ile Arg Ala Gly
    210                 215                 220

Phe Glu Thr Leu Val Glu Ala Gly Tyr Pro Pro Glu Met Ala Tyr Phe
225                 230                 235                 240

Glu Thr Val His Glu Val Lys Leu Ile Val Asp Leu Ile Tyr Glu Ala
                245                 250                 255

Gly Leu Lys Gly Met Arg Tyr Ser Ile Ser Asn Thr Ala Glu Tyr Gly
            260                 265                 270

Asp Tyr Thr Arg Gly Asp Leu Ala Val Pro Leu Glu Glu Thr Lys Arg
        275                 280                 285

Arg Met Arg Glu Ile Leu Arg Gln Ile Gln Ser Gly Glu Phe Ala Arg
    290                 295                 300

Glu Trp Met Leu Glu Asn Gln Val Gly Ser Pro Val Leu Glu Ala Asn
305                 310                 315                 320

Arg Lys Arg Trp Ala Ala His Pro Ile Glu Glu Val Gly Ser Arg Leu
                325                 330                 335

Arg Ala Met Met
            340

<210> SEQ ID NO 4
<211> LENGTH: 338
<212> TYPE: PRT
<213> ORGANISM: Artificial Sequence
<220> FEATURE:
<223> OTHER INFORMATION: COMPONENT OF LATTICE

<400> SEQUENCE: 4

```
Met Lys Ile Tyr Tyr Glu His Asp Ala Asp Leu Gly Phe Ile Leu Gly
1               5                   10                  15

Lys Lys Val Ala Val Leu Gly Phe Gly Ser Gln Gly His Ala His Ala
            20                  25                  30

Leu Asn Leu Lys Asp Ser Gly Val Asp Val Arg Val Gly Leu Arg Lys
        35                  40                  45

Gly Ser Arg Ser Trp Glu Lys Ala Glu Ala Gly Leu Arg Val Leu
    50                  55                  60

Pro Val Ala Glu Ala Val Arg Glu Ala Asp Val Val Met Val Leu Leu
65                  70                  75                  80

Pro Asp Glu Lys Gln Ala Gln Val Tyr Arg Glu Glu Val Glu Pro Asn
                85                  90                  95

Leu Lys Glu Gly Gly Ala Leu Ala Phe Ala His Gly Phe Asn Val His
            100                 105                 110

Phe Gly Gln Ile Lys Pro Arg Lys Asp Leu Asp Val Trp Met Val Ala
        115                 120                 125

Pro Lys Gly Arg Pro Pro Pro Pro Trp Ser His Pro Gln Phe
    130                 135                 140

Glu Lys Pro Pro Pro Pro Pro Pro Pro Gly Ser Gly Val Pro
145                 150                 155                 160

Ala Leu Val Ala Val His Gln Asp Ala Ser Gly Ser Ala Phe Pro Thr
                165                 170                 175

Ala Leu Ala Tyr Ala Lys Ala Ile Gly Ala Ala Arg Ala Gly Val Ile
            180                 185                 190

Ala Thr Thr Phe Lys Asp Glu Thr Glu Thr Asp Leu Phe Gly Glu Gln
        195                 200                 205

Ala Val Leu Cys Gly Gly Leu Thr Arg Leu Ile Arg Ala Gly Phe Glu
    210                 215                 220

Thr Leu Val Glu Ala Gly Tyr Pro Pro Glu Met Ala Tyr Phe Glu Thr
225                 230                 235                 240

Val His Glu Val Lys Leu Ile Val Asp Leu Ile Tyr Glu Ala Gly Leu
                245                 250                 255

Lys Gly Met Arg Tyr Ser Ile Ser Asn Thr Ala Glu Tyr Gly Asp Tyr
            260                 265                 270

Thr Arg Gly Asp Leu Ala Val Pro Leu Glu Glu Thr Lys Arg Arg Met
        275                 280                 285

Arg Glu Ile Leu Arg Gln Ile Gln Ser Gly Glu Phe Ala Arg Glu Trp
    290                 295                 300

Met Leu Glu Asn Gln Val Gly Ser Pro Val Leu Glu Ala Asn Arg Lys
305                 310                 315                 320

Arg Trp Ala Ala His Pro Ile Glu Glu Val Gly Ser Arg Leu Arg Ala
                325                 330                 335

Met Met
```

<210> SEQ ID NO 5
<211> LENGTH: 332
<212> TYPE: PRT
<213> ORGANISM: Artificial Sequence

<220> FEATURE:
<223> OTHER INFORMATION: COMPONENT OF LATTICE

<400> SEQUENCE: 5

```
Met Lys Ile Tyr Tyr Glu His Asp Ala Asp Leu Gly Phe Ile Leu Gly
1               5                   10                  15

Lys Lys Val Ala Val Leu Gly Phe Gly Ser Gln Gly His Ala His Ala
            20                  25                  30

Leu Asn Leu Lys Asp Ser Gly Val Asp Val Arg Val Gly Leu Arg Lys
            35                  40                  45

Gly Ser Arg Ser Trp Glu Lys Ala Glu Ala Gly Leu Arg Val Leu
50                  55                  60

Pro Val Ala Glu Ala Val Arg Glu Ala Asp Val Val Met Val Leu Leu
65                  70                  75                  80

Pro Asp Glu Lys Gln Ala Gln Val Tyr Arg Glu Glu Val Glu Pro Asn
            85                  90                  95

Leu Lys Glu Gly Gly Ala Leu Ala Phe Ala His Gly Phe Asn Val His
            100                 105                 110

Phe Gly Gln Ile Lys Pro Arg Lys Asp Leu Asp Val Trp Met Val Ala
            115                 120                 125

Pro Lys Gly Arg Pro Pro Pro Pro Trp Ser His Pro Gln Phe Glu
130                 135                 140

Lys Arg Pro Pro Gly Gly Ser Gly Val Pro Ala Leu Val Ala Val His
145                 150                 155                 160

Gln Asp Ala Ser Gly Ser Ala Phe Pro Thr Ala Leu Ala Tyr Ala Lys
            165                 170                 175

Ala Ile Gly Ala Ala Arg Ala Gly Val Ile Ala Thr Thr Phe Lys Asp
            180                 185                 190

Glu Thr Glu Thr Asp Leu Phe Gly Glu Gln Ala Val Leu Cys Gly Gly
            195                 200                 205

Leu Thr Arg Leu Ile Arg Ala Gly Phe Glu Thr Leu Val Glu Ala Gly
210                 215                 220

Tyr Pro Pro Glu Met Ala Tyr Phe Glu Thr Val His Glu Val Lys Leu
225                 230                 235                 240

Ile Val Asp Leu Ile Tyr Glu Ala Gly Leu Lys Gly Met Arg Tyr Ser
            245                 250                 255

Ile Ser Asn Thr Ala Glu Tyr Gly Asp Tyr Thr Arg Gly Asp Leu Ala
            260                 265                 270

Val Pro Leu Glu Glu Thr Lys Arg Arg Met Arg Glu Ile Leu Arg Gln
            275                 280                 285

Ile Gln Ser Gly Glu Phe Ala Arg Glu Trp Met Leu Glu Asn Gln Val
            290                 295                 300

Gly Ser Pro Val Leu Glu Ala Asn Arg Lys Arg Trp Ala Ala His Pro
305                 310                 315                 320

Ile Glu Glu Val Gly Ser Arg Leu Arg Ala Met Met
            325                 330
```

<210> SEQ ID NO 6
<211> LENGTH: 337
<212> TYPE: PRT
<213> ORGANISM: Artificial Sequence
<220> FEATURE:
<223> OTHER INFORMATION: COMPONENT OF LATTICE

```
<400> SEQUENCE: 6

Met Lys Ile Tyr Tyr Glu His Asp Ala Asp Leu Gly Phe Ile Leu Gly
1               5                   10                  15

Lys Lys Val Ala Val Leu Gly Phe Gly Ser Gln Gly His Ala His Ala
                20                  25                  30

Leu Asn Leu Lys Asp Ser Gly Val Asp Val Arg Val Gly Leu Arg Lys
            35                  40                  45

Gly Ser Arg Ser Trp Glu Lys Ala Glu Ala Gly Leu Arg Val Leu
    50                  55                  60

Pro Val Ala Glu Ala Val Arg Glu Ala Asp Val Val Met Val Leu Leu
65                  70                  75                  80

Pro Asp Glu Lys Gln Ala Gln Val Tyr Arg Glu Val Glu Pro Asn
                85                  90                  95

Leu Lys Glu Gly Gly Ala Leu Ala Phe Ala His Gly Phe Asn Val His
                100                 105                 110

Phe Gly Gln Ile Lys Pro Arg Lys Asp Leu Asp Val Trp Met Val Ala
                115                 120                 125

Pro Lys Gly Pro Gly His Leu Val Arg Ser Glu Tyr Val Gly Gly Gly
130                 135                 140

Gly Ser His Pro Gln Phe Glu Gly Gly Gly Ser Gly Val Pro Ala
145                 150                 155                 160

Leu Val Ala Val His Gln Asp Ala Ser Gly Ser Ala Phe Pro Thr Ala
                165                 170                 175

Leu Ala Tyr Ala Lys Ala Ile Gly Ala Ala Arg Ala Gly Val Ile Ala
                180                 185                 190

Thr Thr Phe Lys Asp Glu Thr Glu Thr Asp Leu Phe Gly Glu Gln Ala
                195                 200                 205

Val Leu Cys Gly Gly Leu Thr Arg Leu Ile Arg Ala Gly Phe Glu Thr
                210                 215                 220

Leu Val Glu Ala Gly Tyr Pro Pro Glu Met Ala Tyr Phe Glu Thr Val
225                 230                 235                 240

His Glu Val Lys Leu Ile Val Asp Leu Ile Tyr Glu Ala Gly Leu Lys
                245                 250                 255

Gly Met Arg Tyr Ser Ile Ser Asn Thr Ala Glu Tyr Gly Asp Tyr Thr
                260                 265                 270

Arg Gly Asp Leu Ala Val Pro Leu Glu Glu Thr Lys Arg Arg Met Arg
                275                 280                 285

Glu Ile Leu Arg Gln Ile Gln Ser Gly Glu Phe Ala Arg Glu Trp Met
                290                 295                 300

Leu Glu Asn Gln Val Gly Ser Pro Val Leu Glu Ala Asn Arg Lys Arg
305                 310                 315                 320

Trp Ala Ala His Pro Ile Glu Glu Val Gly Ser Arg Leu Arg Ala Met
                325                 330                 335

Met

<210> SEQ ID NO 7
<211> LENGTH: 338
<212> TYPE: PRT
<213> ORGANISM: Artificial Sequence
<220> FEATURE:
<223> OTHER INFORMATION: COMPONENT OF LATTICE
```

<400> SEQUENCE: 7

```
Met Lys Ile Tyr Tyr Glu His Asp Ala Asp Leu Gly Phe Ile Leu Gly
1               5                   10                  15

Lys Lys Val Ala Val Leu Gly Phe Gly Ser Gln Gly His Ala His Ala
            20                  25                  30

Leu Asn Leu Lys Asp Ser Gly Val Asp Val Arg Val Gly Leu Arg Lys
        35                  40                  45

Gly Ser Arg Ser Trp Glu Lys Ala Glu Ala Gly Leu Arg Val Leu
    50                  55                  60

Pro Val Ala Glu Ala Val Arg Glu Ala Asp Val Val Met Val Leu Leu
65                  70                  75                  80

Pro Asp Glu Lys Gln Ala Gln Val Tyr Arg Glu Val Glu Pro Asn
                85                  90                  95

Leu Lys Glu Gly Gly Ala Leu Ala Phe Ala His Gly Phe Asn Val His
                100                 105                 110

Phe Gly Gln Ile Lys Pro Arg Lys Asp Leu Asp Val Trp Met Val Ala
            115                 120                 125

Pro Lys Gly Pro Gly His Leu Val Arg Ser Glu Tyr Val Gly Gly Gly
        130                 135                 140

Gly Ser His Pro Gln Phe Glu Gly Gly Gly Gly Ser Gly Val Pro
145                 150                 155                 160

Ala Leu Val Ala Val His Gln Asp Ala Ser Gly Ser Ala Phe Pro Thr
                165                 170                 175

Ala Leu Ala Tyr Ala Lys Ala Ile Gly Ala Ala Arg Ala Gly Val Ile
                180                 185                 190

Ala Thr Thr Phe Lys Asp Glu Thr Glu Thr Asp Leu Phe Gly Glu Gln
            195                 200                 205

Ala Val Leu Cys Gly Gly Leu Thr Arg Leu Ile Arg Ala Gly Phe Glu
        210                 215                 220

Thr Leu Val Glu Ala Gly Tyr Pro Pro Glu Met Ala Tyr Phe Glu Thr
225                 230                 235                 240

Val His Glu Val Lys Leu Ile Val Asp Leu Ile Tyr Glu Ala Gly Leu
                245                 250                 255

Lys Gly Met Arg Tyr Ser Ile Ser Asn Thr Ala Glu Tyr Gly Asp Tyr
                260                 265                 270

Thr Arg Gly Asp Leu Ala Val Pro Leu Glu Glu Thr Lys Arg Arg Met
            275                 280                 285

Arg Glu Ile Leu Arg Gln Ile Gln Ser Gly Glu Phe Ala Arg Glu Trp
        290                 295                 300

Met Leu Glu Asn Gln Val Gly Ser Pro Val Leu Glu Ala Asn Arg Lys
305                 310                 315                 320

Arg Trp Ala Ala His Pro Ile Glu Glu Val Gly Ser Arg Leu Arg Ala
                325                 330                 335

Met Met
```

<210> SEQ ID NO 8
<211> LENGTH: 3631
<212> TYPE: DNA
<213> ORGANISM: Artificial Sequence
<220> FEATURE:
<223> OTHER INFORMATION: PLASMID

<400> SEQUENCE: 8

```
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccggtaccat gaagatttac     240
tacgagcacg acgcggacct tggcttcatc ctgggcaaga aggtggcggt cttgggcttc     300
ggctcccagg ggcacgccca cgccctgaac ctcaaggact cggggtgga cgtgcgcgtg      360
ggcctgcgca aagggtctag gagctgggag aaggcggagg ccgccgggct tagggtcctc     420
cccgtggccg aggcggtgcg ggaggccgac gtcgtcatgg tcctcctccc cgacgagaag     480
caggcccagg tctaccggga ggaggtggag cccaacctca aggagggcgg ggccctggcc     540
ttcgcccacg gcttcaacgt ccacttcggc cagatcaagc cccgcaagga cctggacgtc     600
tggatggtgg cccccaaggg cccgggccac ctggtgcgct cggagtacgg cggcggatcg     660
aactggagcc atccgcagtt tgaaaagcga ccccctggtg gaagcggggt cccggccctc     720
gtggccgtgc accaggacgc ctcgggaagc gccttcccca ccgccctcgc ctacgccaag     780
gccatcgggg cggcccggc cggggtcatc gccaccacct tcaaggacga gacggagacg      840
gacctcttcg gggagcaggc ggtgctttgc gggggctca cccggctcat ccgggcgggg      900
tttgagaccc tggtggaggc gggctacccc ccggagatgg cctactttga gaccgtccac     960
gaggtgaagc tcatcgtgga cctcatctac gaggcggggc ttaaggggat gcgctactcc    1020
atctccaaca ccgccgagta cggggactac acccggggcg acctcgccgt gcccctggag    1080
gagaccaagc gccgcatgcg ggagatcctg cgccagatcc agtccgggga gttcgcccgg    1140
gagtggatgc tggagaacca ggtgggaagc cccgtcctgg aggccaaccg caagcgctgg    1200
gcggcccacc ccattgagga ggtgggctcg aggcttcgcg ccatgatgag atcttaagcg    1260
tggcgccatc cgcagtttgg tgggtaaggc cgcgactcta gaattccaac tgagcgccgg    1320
tcgctaccat taccaacttg tctggtgtca aaaataatag gcctactagt cggccgtacg    1380
ggcccctttcg tctcgcgcgt ttcggtgatg acggtgaaaa cctctgacac atgcagctcc    1440
cggagacggt cacagcttgt ctgtaagcgg atgccgggag cagacaagcc cgtcagggcg    1500
cgtcagcggg tgttggcggg tgtcggggct ggcttaacta tgcggcatca gagcagattg    1560
tactgagagt gcaccatatg cggtgtgaaa taccgcacag atgcgtaagg agaaaatacc    1620
gcatcaggcg gccttaaggg cctcgtgata cgcctatttt tataggttaa tgtcatgata    1680
ataatggttt cttagacgtc aggtggcact tttcgggaa atgtgcgcgg aaccccctatt    1740
tgtttatttt tctaaataca ttcaaatatg tatccgctca tgagacaata accctgataa    1800
atgcttcaat aatattgaaa aaggaagagt atgagtattc aacatttccg tgtcgccctt    1860
attccctttt ttgcggcatt ttgccttcct gtttttgctc acccagaaac gctggtgaaa    1920
gtaaaagatg ctgaagatca gttgggtgca cgagtgggtt acatcgaact ggatctcaac    1980
agcggtaaga tccttgagag ttttcgcccc gaagaacgtt ttccaatgat gagcactttt    2040
aaagttctgc tatgtggcgc ggtattatcc cgtattgacg ccgggcaaga gcaactcggt    2100
cgccgcatac actattctca gaatgacttg gttgagtact caccagtcac agaaaagcat    2160
cttacggatg gcatgacagt aagagaatta tgcagtgctg ccataaccat gagtgataac    2220
actgcggcca acttacttct gacaacgatc ggaggaccga aggagctaac cgcttttttg    2280
cacaacatgg gggatcatgt aactcgcctt gatcgttggg aaccggagct gaatgaagcc    2340
```

-continued

```
ataccaaacg acgagcgtga caccacgatg cctgtagcaa tggcaacaac gttgcgcaaa    2400
ctattaactg gcgaactact tactctagct tcccggcaac aattaataga ctggatggag    2460
gcggataaag ttgcaggacc acttctgcgc tcggcccttc cggctggctg gtttattgct    2520
gataaatctg gagccggtga gcgtgggtct cgcggtatca ttgcagcact ggggccagat    2580
ggtaagccct cccgtatcgt agttatctac acgacgggga gtcaggcaac tatggatgaa    2640
cgaaatagac agatcgctga gataggtgcc tcactgatta gcattggta actgtcagac    2700
caagtttact catatatact ttagattgat ttaaaacttc atttttaatt taaaaggatc    2760
taggtgaaga tccttttttga taatctcatg accaaaatcc cttaacgtga gttttcgttc    2820
cactgagcgt cagaccccgt agaaaagatc aaaggatctt cttgagatcc ttttttttctg    2880
cgcgtaatct gctgcttgca acaaaaaaaa ccaccgctac cagcggtggt ttgtttgccg    2940
gatcaagagc taccaactct ttttccgaag gtaactggct tcagcagagc gcagatacca    3000
aatactgtcc ttctagtgta gccgtagtta ggccaccact tcaagaactc tgtagcaccg    3060
cctacatacc tcgctctgct aatcctgtta ccagtggctg ctgccagtgg cgataagtcg    3120
tgtcttaccg ggttggactc aagacgatag ttaccggata aggcgcagcg gtcgggctga    3180
acggggggtt cgtgcacaca gcccagcttg gagcgaacga cctacaccga actgagatac    3240
ctacagcgtg agctatgaga aagcgccacg cttcccgaag ggagaaaggc ggacaggtat    3300
ccggtaagcg gcagggtcgg aacaggagag cgcacgaggg agcttccagg gggaaacgcc    3360
tggtatcttt atagtcctgt cgggtttcgc cacctctgac ttgagcgtcg attttttgtga    3420
tgctcgtcag gggggcggag cctatggaaa aacgccagca acgcggcctt tttacggttc    3480
ctggccttttt gctggccttt tgctcacatg ttctttcctg cgttatcccc tgattctgtg    3540
gataaccgta ttaccgcctt tgagtgagct gataccgctc gccgcagccg aacgaccgag    3600
cgcagcgagt cagtgagcga ggaagcggaa g                                   3631
```

<210> SEQ ID NO 9
<211> LENGTH: 8
<212> TYPE: PRT
<213> ORGANISM: Artificial Sequence
<220> FEATURE:
<223> OTHER INFORMATION: BINDING PEPTIDE

<400> SEQUENCE: 9

Trp Ser His Pro Gln Ser Glu Lys
1               5

<210> SEQ ID NO 10
<211> LENGTH: 9
<212> TYPE: PRT
<213> ORGANISM: Artificial Sequence
<220> FEATURE:
<223> OTHER INFORMATION: BINDING PEPTIDE

<400> SEQUENCE: 10

Asn Trp Ser His Pro Gln Phe Glu Lys
1               5

<210> SEQ ID NO 11
<211> LENGTH: 9
<212> TYPE: PRT
<213> ORGANISM: Artificial Sequence
<220> FEATURE:
<223> OTHER INFORMATION: BINDING PEPTIDE

```
<400> SEQUENCE: 11

Pro Trp Ser His Pro Gln Phe Glu Lys
1               5

<210> SEQ ID NO 12
<211> LENGTH: 9
<212> TYPE: PRT
<213> ORGANISM: Artificial Sequence
<220> FEATURE:
<223> OTHER INFORMATION: BINDING PEPTIDE

<400> SEQUENCE: 12

Gly Gly Ser His Pro Gln Phe Glu Gly
1               5

<210> SEQ ID NO 13
<211> LENGTH: 9
<212> TYPE: PRT
<213> ORGANISM: Artificial Sequence
<220> FEATURE:
<223> OTHER INFORMATION: BINDING PEPTIDE
<220> FEATURE:
<221> NAME/KEY: MISC_FEATURE
<222> LOCATION: (1)..(1)
<223> OTHER INFORMATION: N OR G
<220> FEATURE:
<221> NAME/KEY: MISC_FEATURE
<222> LOCATION: (2)..(2)
<223> OTHER INFORMATION: W OR G
<220> FEATURE:
<221> NAME/KEY: MISC_FEATURE
<222> LOCATION: (7)..(7)
<223> OTHER INFORMATION: S OR F
<220> FEATURE:
<221> NAME/KEY: MISC_FEATURE
<222> LOCATION: (9)..(9)
<223> OTHER INFORMATION: K OR G

<400> SEQUENCE: 13

Xaa Xaa Ser His Pro Gln Xaa Glu Xaa
1               5

<210> SEQ ID NO 14
<211> LENGTH: 4
<212> TYPE: PRT
<213> ORGANISM: Artificial Sequence
<220> FEATURE:
<223> OTHER INFORMATION: LINKER

<400> SEQUENCE: 14

Gly Gly Gly Ser
1

<210> SEQ ID NO 15
<211> LENGTH: 4
<212> TYPE: PRT
<213> ORGANISM: Artificial Sequence
<220> FEATURE:
<223> OTHER INFORMATION: LINKER

<400> SEQUENCE: 15

Pro Gly Gly Gly
1

<210> SEQ ID NO 16
<211> LENGTH: 6
<212> TYPE: PRT
<213> ORGANISM: Artificial Sequence
```

```
<220> FEATURE:
<223> OTHER INFORMATION: LINKER

<400> SEQUENCE: 16

Arg Pro Pro Pro Pro Pro
1               5

<210> SEQ ID NO 17
<211> LENGTH: 5
<212> TYPE: PRT
<213> ORGANISM: Artificial Sequence
<220> FEATURE:
<223> OTHER INFORMATION: LINKER

<400> SEQUENCE: 17

Arg Pro Pro Pro Pro
1               5

<210> SEQ ID NO 18
<211> LENGTH: 4
<212> TYPE: PRT
<213> ORGANISM: Artificial Sequence
<220> FEATURE:
<223> OTHER INFORMATION: LINKER

<400> SEQUENCE: 18

Arg Pro Pro Gly
1

<210> SEQ ID NO 19
<211> LENGTH: 4
<212> TYPE: PRT
<213> ORGANISM: Artificial Sequence
<220> FEATURE:
<223> OTHER INFORMATION: LINKER

<400> SEQUENCE: 19

Pro Pro Pro Pro
1

<210> SEQ ID NO 20
<211> LENGTH: 9
<212> TYPE: PRT
<213> ORGANISM: Artificial Sequence
<220> FEATURE:
<223> OTHER INFORMATION: LINKER

<400> SEQUENCE: 20

Pro Pro Pro Pro Pro Pro Pro Pro Pro
1               5

<210> SEQ ID NO 21
<211> LENGTH: 127
<212> TYPE: PRT
<213> ORGANISM: Artificial Sequence
<220> FEATURE:
<223> OTHER INFORMATION: COMPONENT OF LATTICE

<400> SEQUENCE: 21

Ala Glu Ala Gly Ile Thr Gly Thr Trp Tyr Asn Gln Leu Gly Ser Thr
1               5                   10                  15

Phe Ile Val Thr Ala Gly Ala Asp Gly Ala Leu Thr Gly Thr Tyr Glu
                20                  25                  30

Ser Ala Val Gly Asn Ala Glu Ser Arg Tyr Val Leu Thr Gly Arg Tyr
            35                  40                  45
```

```
Asp Ser Ala Pro Ala Thr Asp Gly Ser Gly Thr Ala Leu Gly Trp Thr
    50                  55                  60
Val Ala Trp Lys Asn Asn Tyr Arg Asn Ala His Ser Ala Thr Thr Trp
65              70                  75                  80
Ser Gly Gln Tyr Val Gly Gly Ala Glu Ala Arg Ile Asn Thr Gln Trp
                85                  90                  95
Leu Leu Thr Ser Gly Thr Thr Glu Ala Asn Ala Trp Lys Ser Thr Leu
                100                 105                 110
Val Gly His Asp Thr Phe Thr Lys Val Lys Pro Ser Ala Ala Ser
                115                 120                 125

<210> SEQ ID NO 22
<211> LENGTH: 4
<212> TYPE: PRT
<213> ORGANISM: Artificial Sequence
<220> FEATURE:
<223> OTHER INFORMATION: BINDING MOTIF

<400> SEQUENCE: 22

Ser His Pro Gln
1

<210> SEQ ID NO 23
<211> LENGTH: 4
<212> TYPE: PRT
<213> ORGANISM: Artificial Sequence
<220> FEATURE:
<223> OTHER INFORMATION: LINKER

<400> SEQUENCE: 23

Pro Gly Gly Ser
1
```